United States Patent [19]

Klement et al.

[11] Patent Number: 4,776,853
[45] Date of Patent: Oct. 11, 1988

[54] PROCESS FOR PREPARING BIOLOGICAL MAMMALIAN IMPLANTS

[75] Inventors: Petr Klement; Gregory J. Wilson, both of Toronto; Herman Yeger, Richmond Hill, all of Canada

[73] Assignee: HSC Research Development Corporation, Toronto, Canada

[21] Appl. No.: 77,753

[22] Filed: Jul. 27, 1987

[30] Foreign Application Priority Data

Jul. 28, 1986 [GB] United Kingdom ................. 8618374

[51] Int. Cl.$^4$ .............................................. A61F 1/22
[52] U.S. Cl. ......................................... 8/94.11; 623/1
[58] Field of Search ..................... 8/94.11; 623/1, 1.4, 623/1.5

[56] References Cited

U.S. PATENT DOCUMENTS

| 4,323,358 | 4/1982 | Lentz et al. | 8/94.11 |
| 4,352,887 | 10/1982 | Reid et al. | 8/94.11 |
| 4,378,224 | 3/1983 | Nimni et al. | 8/94.11 |
| 4,553,974 | 11/1985 | Dewanjee | 8/94.11 |

FOREIGN PATENT DOCUMENTS 8404880  5/1984  PCT Int'l Appl. .

Primary Examiner—A. Lionel Clingman
Assistant Examiner—John F. McNally
Attorney, Agent, or Firm—Banner, Birch, McKie and Beckett

[57] ABSTRACT

A process for preparing biological material for implant in mammal's cardiovascular system, respiratory system or soft tissue is disclosed. The process comprises:

(1) isolating from a suitable donor a desired tissue sample of the biological material;
(2) extracting the tissue sample with an hypotonic buffer solution at a mild alkaline pH, the buffer solution including active amounts of proteolytic inhibitors and antibiotics;
(3) extracting the tissue sample with a buffered solution having a high concentration of salt, the solution being at a mild alkaline pH and including a non-ionic detergent with protease inhibitors and antibiotics;
(4) subjecting tissue sample to enzymatic digestion in a buffered saline solution, the enzymes consisting of purified protease-free dioxyribonuclease and ribonuclease;
(5) extracting the tissue sample with an anionic detergent at a mild alkaline pH; and
(6) storing the tissue sample in physiologic buffered solutions.

15 Claims, 2 Drawing Sheets

PROCESS FOR PREPARING BIOLOGICAL MAMMALIAN IMPLANTS

FIELD OF THE INVENTION

This invention relates to implantable prostheses for replacement of mammalian tissue including arteries, veins, valves and the like, and more particularly to prostheses made from biological material.

BACKGROUND OF THE INVENTION

Over the past three decades, numerous different types of vascular prostheses have been produced for the replacement of arteries and veins. Reasonable success has been achieved with large caliber vascular prostheses (greater than 6 mm internal diameter) using man-made polymers, notably Dacron and Teflon in both knitted and woven configurations. Expanded polytetrafluoroethylene grafts have, to date, been the most successful of commercially available vascular prostheses in smaller caliber (4-6 mm) configurations, but it is fair to say that further improvements are necessary to produce a small caliber vascular prosthesis which can really challenge autologous saphenous vein for overall efficacy in both the peripheral vascular and coronary locations.

Biological vascular grafts represent the most effective alternative design pathway. With few exceptions, biological prostheses have been produced by methods which incorporated either proteolytic enzyme digestion followed by aldehyde fixation or aldehyde fixation alone. In some cases, further surface modifications were performed with a variety of chemicals to modify surface charge. The objectives were to stabilize tissues by crosslinking the proteinaceous components and to alter favorably the thrombogenic properties of the vessels. In all instances where aldehyde fixation was used the resultant vessel was altered considerably with respect to its mechanical properties. Fixation, however, appeared to render these vessels less antigenic. In the case of heart valves, previously fixed with aldehydes, further treatment with an anionic detergent, sodium dodecyl sulfate, substantially reduced the tendency of these devices to undergo calcification as disclosed in U.S. Pat. No. 4,323,358. Inhibition of calcification has also been attempted by incorporating a variety of inhibitors such as diphosphonates or chondroitan sulfates, as disclosed in U.S. Pat. Nos. 4,378,224 and 4,553,974. Both non-ionic and ionic detergents have been used in other ways, for example, to clear tissues of soluble materials prior to further treatment with aldehydes.

None of the treatments described above provided superior performance to that which would be achieved in blood vessel replacements, with artificial entirely man-made materials (eg. polytetrafluoroethylene). In contrast, biological valve replacements have an appreciably better record of performance than prostheses from synthetic materials. A new approach is based upon the realization that the extracellular matrix (which is produced by connective tissue cells, the major cell component of vessels) provides the vessel with inherent mechanical properties, forms a highly integrated and dense network of crosslinked fibers and is essentially resistant to extraction by detergents and physiological solutions.

The advantages of retaining intact this extracellular matrix, composed primarily of a collagenous component but also including elastin and other tightly bound substances, has been explored by Klaus, B. and Duhamel, R. (WO 84/0488)) for the production of sterile body implants. In their method, a variety of tissues were extracted sequentially with non-ionic and ionic detergents to yield structures essentially free of cellular membranes, nucleic acids, lipids and cytoplasmic components. Dependent upon the particular application, these structures were further modified by fixation and/or surface modification. In the case of canine carotid arteries, treated with their protocol, they achieved acceptable results after 90 days post-implantation.

Healthy arteries or veins should provide material most suitable for the replacement of damaged vessels in terms of biological and mechanical properties.

An extraction protocol has been developed which provides substantially improved biological protheses which are highly biocompatible and long lasting replacements. The biological prosthesis is equivalent in compliance and mechanical strength to a healthy vessel through retention of elastic properties and highly resistant to calcification and thrombogenesis and hence in most situations, avoids the need to administer anti-thrombosis drugs.

Accordingly, the invention removes soluble small and high molecular weight substances from natural tissue which will be used as the prosthesis while retaining the insoluble, collagenous and elastic "backbone" of the natural tissue. The tissue is extracted by a series of detergent and non-proteolytic enzymatic treatments.

SUMMARY OF THE INVENTION

According to an aspect of the invention, a process for preparing biological material for implant in a mammalian cardiovascular system, respiratory system or soft tissue removes cellular membranes, nucleic acids, lipids and cytoplasmic components and forms an extra cellular matrix having as major components collagens and elastins. The process comprises the following steps:
(1) isolating from a suitable donor a desired tissue sample of the biological material;
(2) extracting the tissue sample with a hypotonic buffer solution at a mild alkaline pH for rupturing cells of the tissue sample, the hypotonic buffer solution including active amounts of proteolytic inhibitors and active amounts of antibiotic;
(3) extracting the tissue sample with a buffered solution having a high concentration of salt, the solution being at a mild alkaline pH and including a non-ionic detergent and protease inhibitors and phenylmethylsulfonylfluoride and active amounts of antibiotic;
(4) subjecting the tissue sample to enzymatic digestion in a buffered saline solution, said enzymes consisting of purified protease-free deoxyribonuclease and ribonuclease;
(5) extracting the tissue sample with an anionic detergent at a mild alkaline pH, and
(6) storing the processed tissue sample in physiologic saline.

BRIEF DESCRIPTION OF THE DRAWINGS

Preferred embodiments of the invention are shown in the drawings, wherein.

DETAILED DESCRIPTION OF THE PREFERRED EMBODIMENTS

Figure 1:
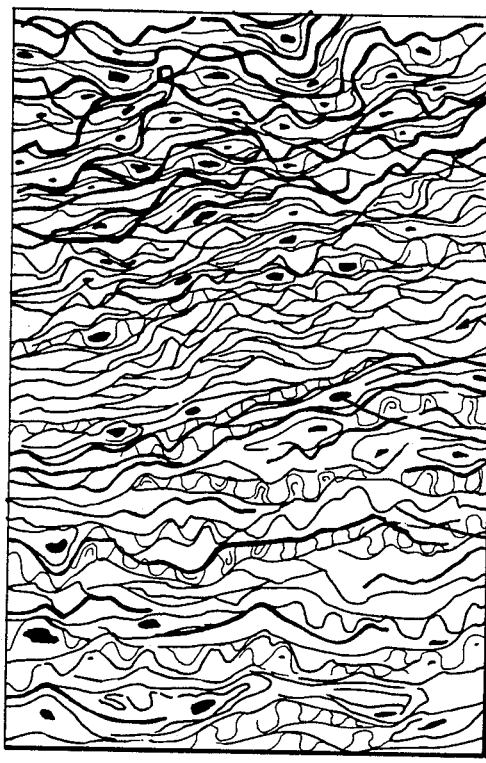
FIG. 1 is a view of unprocessed iliac artery examined with H and E staining.

This invention is based upon the rationale that healthy arteries and veins and other relevant tissue should provide the ideal replacement vessel since they would be a structure most biologically equivalent to the damaged vessel in terms of size, shape, mechanical properties and biochemistry. The components of the vessels that are nearly equivalent are the interstitial collagens, elastin and glycosaminoglycans. All other components including cell membranes, cytoplasm, nuclear material and serum components could initiate an immunological rejection response and, therefore, necessitate complete removal. These latter components contribute only in a minor way to the mechanical properties of the vessel, so that, if the collagenous and elastic fraction can be retained intact and in its natural state, the mechanical properties would be essentially the same as the normal vessel. Because such a processed vessel could be recellularized by host connective tissue cells, due to its biomatrix properties, it has the potential to provide optimal patency, healing characteristics and durability.

In the procedure, normal healthy vessels are surgically removed, cleaned to remove extraneous matter and immediately submersed in the first extraction solution which consists of a hypotonic buffer containing suitable protease inhibitors and antibiotics. The vessels are subsequently enclosed within a nylon or polyester mesh, so as to form a chamber, and extracted with the first solution, as above, for an additional 24 to 48 hours within a cylinder, and stirred at 2° to 10° C. The hypotonic condition allows the extraction to be initiated since cells are ruptured. In the second step, the vessels are subjected to a buffered high salt solution containing a non-ionic detergent, protease inhibitors and antibiotics. This step is also carried out for 24 to 48 hours at 2° to 10° C. under stirring. Both the high salt and detergent permit extraction of cytoplasmic components and soluble extracellular matrix components, but keep the rest of the extracellular matrix in an intact state. The carrying out of these steps at the lower temperatures inhibits autoproteolysis. This high salt/detergent step is followed by several distilled water washes and equilibration with a buffered saline solution for the enzymatic portion of the procedure. The enzymes used are a mixture of purified, protease free, deoxyribonuclease and ribonuclease since both are required to remove nuclear material. It is also the advantage of such a combination that entrapped foreign agents such as bacteria and viruses would also be susceptible to these enzymes. This enzyme digestion is carried out with reciprocal shaking at preferably 37° C. (range 35° to 38° C.) for typically 2 to 12 hours, but more usually 4 to 6 hours, dependent on vessel size. In the last step of the extraction protocol, the vessels are extracted with an anionic detergent at alkaline pH. This anionic detergent extraction is carried out at ambient temperatures with stirring for 24 to 48 hours including a change to fresh solution approximately halfway through. After the anionic detergent step, the vessels are washed under stirring with large volumes of distilled water and finally stored in physiologic saline containing antibiotics.

It is appreciated that a variety of protease inhibitors and antibiotics may be used. Possible protease inhibitors include phenylmethylsulfonylfloride, diisopropyl phosphofluoridate, ethylenediaminetetraacetic acid, ethylene glycol-bis($\beta$-aminoethylether)N,N,N'N'-tetreaacetic acid and N-ethylmaleimide. The working range of these inhibitors is from 1 $\mu$M to 25 mM dependent upon inhibitor used. The preferred inhibitors are ethylenediaminetetraacetic acid and phenylmethylsulfonylfluoride. Useful gram (+ve) and gram (−ve) or broad spectrum antibiotics include synthetic and semi-synthetic penicillins, streptomycin, gentamycin and cephalosporins. The preferred antibiotics are penicillins and streptomycin.

According to a preferred embodiment of this invention, the non-ionic detergent may be selected from the following group TRITON X-100 (trademark), am octylphenoxy polyethoxyethanol, manufactured by Rohm and Haas; BRIJ-35 (trademark), a polyethoxyethanol lauryl ether, manufactured by Atlas Chemical Co.; TWEEN 20 (trademark), a polyethoxyethanol sorbitan monolaureate, manufactured by Rohm and Haas; and LUBROL-PX (trademark), a polyethylene lauryl ether, manufactured by Rohm and Hass.

Suitable anionic detergents include those selected from the group consisting of a salt of a sulfated higher aliphatic alcohol, sulfonated alkane and sulfonated alkylarene containing from 7 to 22 carbon atoms in a branched or unbranched chain. The preferred anionic detergent is sodium dodecyl sulphate.

It is appreciated that, when desired, suitable crosslinking agents may be used to induce crosslinking in the resulting collagen and elastin of the treated tissue. Suitable crosslinking agents include glutaraldehyde, carbodiimide and polyglycerol polyglycidyl ether.

It is appreciated that the treatment of this invention may be applied to a variety of sources of suitable tissue extracted from appropriate donors, including bovine, ovine, caprine, porcine and human sources. The tissue samples may include veins, arteries, pericardium, dura mater, ligaments, tendons, trachea and skin. Such components, when treated, may be used for prostheses to replace arteries, veins, heart valves, ligaments and tendons, trachea and skin.

Vessels extracted by the above procedure were analyzed histologically, biochemically and mechanically prior to implantation. The morphology of the extracted vessel reveals the presence of a dense meshwork of collagen and elastin fibers, as seen in non-extracted vessels, but an absence of the cytoplasmic component and the soluble extracellular matrix component (ground substance). Biochemical analysis reveals the retention of collagen, elastin and glycosaminoglycans related to that found in basement membranes while glycosaminoglycans of ground substance have been removed. The lumenal aspect of the vessel, as seen by scanning electron microscopy, shows a smooth membrane-like surface, corresponding to a residual basement membrane, subtended in profile, by a prominent fibrillary component, corresponding to the internal lamina and underlying collagen fibers. The presence of the basal lamina components type IV collagen and laminin on the lumenal surface was confirmed immunohistochemically. Mechanical testing showed that non-extracted and extracted vessels were virtually identical. The extracted sample had a slightly lower stiffness at a given stress, and slightly increased hysteresis losses. These differences were well below the expected experimental accuracy. Similar results were obtained for carotid and iliac artery samples (canine).

Our processed biological vascular grafts implanted as grafts in the femoral and carotid artery sites (15 implants in 8 dogs) as well as the abdominal aorta (1 dog) were evaluated for follow-up periods ranging from 3 to 1361 days, with further follow-up continuing on three of the grafts. All implants were processed canine carotid or iliac arteries with the exception of the aortic interposition graft which was processed aorta. The implants at femoral and common carotid positions were performed with end-to-side anastomoses using grafts of 5 to 8 cm in length and 5 to 6 mm in diameter with the host artery ligated near each anastomosis and divided at the end of the procedure. The dogs used were screened with a range of biochemical and hematological tests so that normal, healthy subjects were chosen. No anticoagulation was employed at any time nor were anti-platelet medications given before, during or after implantation. Graft patency was assessed by palpation and/or angiography. Explantation was scheduled to provide grafts for examination over a range of follow-up intervals, balancing the need for long term follow-up to assess continued patency and the biological fate of the implants with the need for sequential morphological assessment of these implants. Each graft was opened longitudinally, photographed and submitted for evaluation by microscopy, using the same techniques as applied to samples of the biografts prior to implantation.

The following exemplifies preferred embodiments of the invention in preparing vascular grafts and their biological properties. It is appreciated that, although the following examples are directed to vascular grafts, the processes of this invention are equally useful in preparing various type of mammalian implants derived from natural sources, which include arteries, veins, heart valves and the like.

EXAMPLE 1

Details of Extraction Process as Used with Arteries

1. A variety of arteries have been treated: femoral, iliac, carotid, aortic.
2. The vessels are resected and cleaned of adhering connective tissues and debris prior to extraction.
3. Cleaned vessels are immediately placed into the first extraction solution called Solution A, which consists of: 10 mM Tris.HCL, 5 mM EDTA at pH 8.0 supplemented with 50 U/ml penicillin/streptomycin combination (stock of 10,000 U/ml penicillin and 10,000 $\mu$g/ml streptomycin GIBCO) and 1 $\mu$M PMSF (phenylmethylsulfonyl fluoride—an antiproteolytic agent). Extraction is carried out with vessels enclosed in Nitex envelopes in a cylinder at 5° C., with stirring for 24 hours (24 hours to 48 hours).
4. The vessels are placed into the second extraction solution, Solution B consisting of: 50 mM Tris.HCL, 1.5M KCL, 1% Triton X-100 (a non-ionic detergent), 5 mM EDTA at pH 8.0 supplemented with 1 $\mu$M PMSF and 50 U/ml penicillin/streptomycin as in Solution A. Extraction is carried out with vessels in Nitex envelopes in a cylinder at 5° C. with stirring for 24 hours (range of 24 to 72 hours). The volume ratios of solutions A or B to tissue are a minimum of 100:1.
5. The vessels are washed three times in 100:1 volumes of either purified (Milli Q system 0.2 u filtered water or same water after autoclaving) water and then for 30 minutes to 1 hour in Hanks buffered salt solution (GIBCO) containing 10 mM Hepes buffer and 50 U/ml penicillin/streptomycin at 37° with rocking.
6. The vessels are treated enzymatically as follows: The vessels are transferred to solutions containing 0.75 mg/15 ml DNase I (Type III—Sigma) and RNase (Type 1A—Sigma) 1.25 mg/15 ml and rocked for 4 to 6 hours at 37° C.
7. The vessels are washed briefly one time in purified water for 30 minutes or transferred directly to solution C.
8. The vessels are mounted in Nitex envelopes and extracted with Solution C consisting of 50 mM TRIS.HCl at pH 9.0 with 1% SDS (sodium dodecyl sulphate) for 24 hours (range 24 to 96 hours) at ambient temperature.
9. The vessels are washed in >100:1 volumes of water or saline at least three times over 24 hours (range 24 to 96 hours).
10. The vessels are stored in either Hanks buffered salt solution with Hepes (10-25 mM) and penicillin and streptomycin or in phosphate buffered saline with the same antibody at 4° C. The penicillin and streptomycin concentration is raised to 100 U/ml and 100 $\mu$g/ml respectively.

The extraction procedure is initiated by hypotonic lysis of the tissue cells. Antibiotics are included from the onset of the process. No cell poisons, such as azide are used in this process which is initiated by the hypotonic lysis of the tissue cells. A high salt, non-ionic detergent combination is used to extract a substantial proportion of the cytoplasmic components. The high salt solution generally includes a salt concentration in the range of 1 to 2 Molar of the desired salt. In accordance with this Example, the preferred salt is potassium chloride at 1 to 2 Molar, usually 1.5M. This type of salt will not precipitate in colder solutions at the higher concentrations. It is known from cultured cell work that this combination is gentle and leaves behind a cell cytoskeleton but completely permeabolizes the cell. A combined use of DNase and RNase is used under physiologic conditions to remove nuclear material, both enzymes being used together to provide an effective removal.

EXAMPLE 2

Morphology: To assess the cellularity of the graft and the presence of other extractable components, standard histological methods were employed. Unprocessed and processed vessels were fixed in formaldehyde, paraffin embedded and samples stained with hematoxylin and eosin (H and E) for general histology and with the Van Gieson stain for the discrimination of collagen and elastin. To assess the topography of the endothelial side of the graft, grafts were examined with scanning electron microscopy (SEM) using a standard method of preparation. Briefly, tissues were fixed in glutaraldehyde, dehydrated, critical point dried and gold coated and examined in a JEOL 35S scanning electron microscope.

Figure 2:
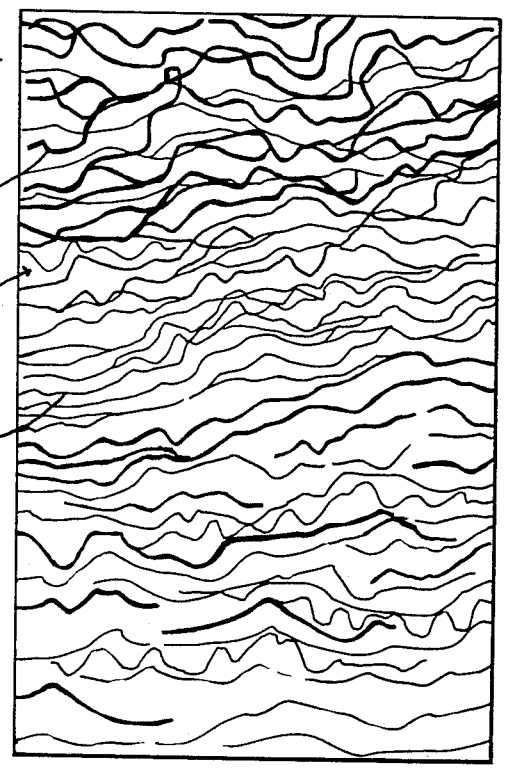
FIG. 2 is a view of the iliac artery of FIG. 1 processed in accordance with this invention and observed with H and E staining.

A photomicrograph of a processed vessel such as a processed aorta revealed a highly uniform intimal surface. H and E staining of a carotid artery (unprocessed) revealed the presence of a normal media rich in smooth muscle cells as shown schematically in FIG. 1. The tissue sample 10 consists of predominantly smooth muscle cells 12, each haing a nucleus 14. The cells are surrounded by collagen bundles and elastic laminae 18. Alternatively, a Van Gieson stain has revealed a prominent array of elastic laminae and a moderate amount of collagen interspersed between the elastic laminae. After processing and staining with H and E stain, FIG. 2 shows schematically that the treated sample 20 has the cellular material removed, leaving behind the collagen 16 and elastin 18. FIG. 2 shows the intact organization of these structures and the appearance of a more open architecture. Scanning electron microscopy of the intima of a processed artery has revealed that the endothelial covering has been removed, leaving behind a substratum which represents the basement membrane. The presence of two basement membrane components, type IV collagen and laminin, was demonstrated by immunofluorescent labelling with specific antibodies. The SEM also revealed the high degree of fibrillar complexity which is present in natural vessels, consisting of fine and course collagen fibers interwoven with elastin.

EXAMPLE 3

Biochemistry: In order to determine the extent to which collagen, elastin and interstitial ground substance (hyaluronic acid, etc.) has been removed during the extraction, vessels were analyzed with biochemical methods. Unprocessed and processed vessels were treated as follows:

(A) Collagen—the acid pepsin soluble fraction was analyzed.

(B) Elastin—the fraction remaining after alkali extraction was analyzed.

(C) Matrix (soluble connective tissue)—no further extraction required, the entire samples were analyzed.

For all three analyses, samples were hydrolyzed in hydrochloric acid and the content of hydroxyproline for (A+B) and N-acetylglucosamine indicative of hyaluronic acid of ground substance and N-acetylgalactosamine indicative of tightly bound glycosaminoglycans of basement membrane for (C) determined. Analyses were performed with a Beckman Amino Acid Analyzer. E-Aminocaproic acid was used as the internal standard. The results are expressed per mg dry weight of vessel.

Arteries before and after processing are compared for their content of collagen, elastin and ground substance in Table 1. The results show: (1) no change in the elastin content; (2) a minimal and insignificant difference in collagen content: and (3) a significant loss of ground substance in processed vessels as indicated by the decrease of N-acetylglucosamine (GlcNac) content. GlcNac is a major component of hyaluronic acid. Loss of glycosaminoglycans would be expected as they are highly soluble. This data demonstrates that processed vessels are essentially free of physiologically soluble substances and cells but retain their network of crosslinked collagen and elastin fibers.

TABLE 1

| Vessel Component | Before Processing | After Processing |
| --- | --- | --- |
| Collagen | 303 µg/mg | 329 µg/mg |
| Elastin | 559 µg/mg | 647 µg/mg |
| Glycosaminoglycans | | |
| GlcNac | 38.16 nM/mg | 0.046 nM/mg |
| GalNac | 17.86 nM/mg | 15.24 nM/mg |
| Units | | |

Nanomolar (nM) per mg dry weight vessel sample.
Microgram (µg) per mg dry weight vessel sample.

It is noted that at least 10% of the dry weight of vessels prior to processing reflects the cellular component which is missing from the processed vessels.

EXAMPLE 4

Mechanical: In this test, stress-strain curves were obtained for unprocessed and processed vessels as follows: Five mm wide circumferential strips were washed three times in Hanks physiological solution and mounted on an Instron TT-C Universal Testing Machine such that each sample could be stretched between the two grips and the resulting load and extension measured. The information was digitized on a Tektronix computer and converted to stress-strain data. Sample dimensions for this analysis were obtained by photographic recording of sample gauge length and mean width and by thickness measurement with a Mitutayo non-rotating thickness gauge. Strip volume was assumed to be constant throughout the test. Final stress-strain curves were plotted by computer.

Figure 3:
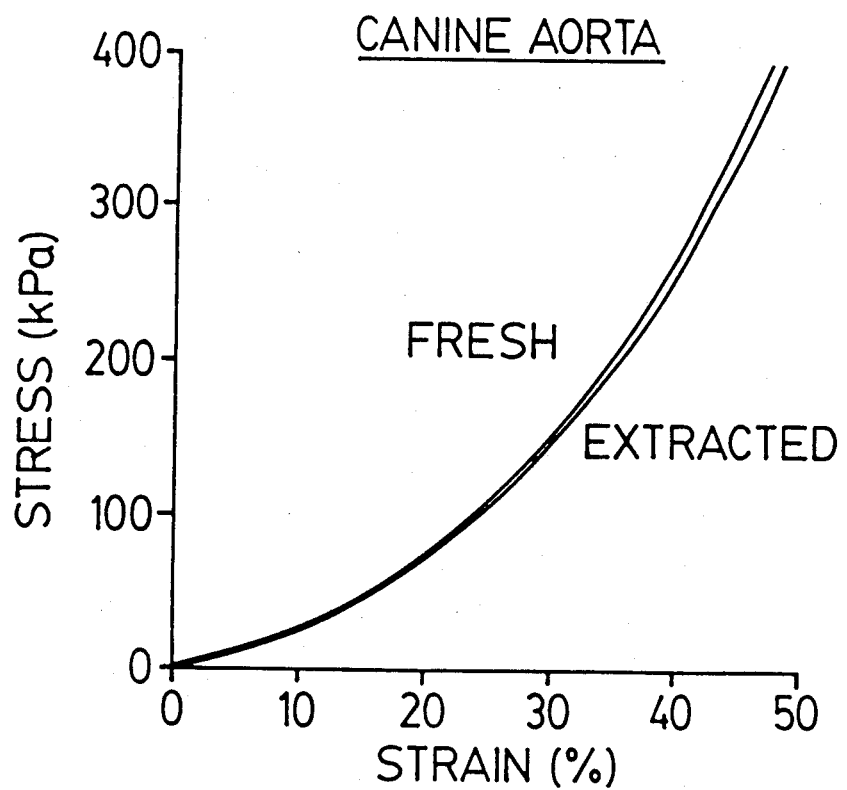
FIG. 3 is a graph comparing physical properties of fresh and processed artery.

FIG. 3 illustrates a typical stress-strain curve for comparison of fresh and extracted aorta. The stress-strain curves obtained for the fresh and extracted samples were virtually identical. The extracted sample showed very slightly lower stiffness at a given stress, and slightly increased hysteresis losses. These differences were well below the expected experimental accuracy. Therefore, in low strain testing, the extraction procedure did not significantly affect mechanical performance of the vessel wall. Similar results were obtained for carotid and iliac artery samples.

EXAMPLE 5

In-Vivo Evaluation

A summary of the status at explanation or on continued follow-up of the 16 grafts is presented in Table 2. Only one of the grafts was occluded with thrombus and this occlusion occurred during the first week, as assessed by palpation, although the graft was not explanted until 185 days post-implantation because of the presence of a patent graft in the contralateral femoral artery.

Of the 15 grafts patent on angiographic evaluation, 13 which were explanted at follow-up intervals of 3 to 484 days and confirmed by direct observation to be widely patent with minimal mural thrombus.

The aortic interposition graft was mainly of interest in regard to possible aneurysm formation. Angiography at three years follow-up revealed no aneurysm formation. All explanted grafts were free of aneurysm formation up to 434 days follow-up and two femoral position grafts evaluated angiographically at 125 days and still being followed up after 856 days are free of aneurysm formation.

Preliminary histological evaluation of the explanted grafts revealed no inflammatory response of the new host to the graft and no calcification.

TABLE 2

SUMMARY OF 16 HSC-PBVG IMPLANTED IN 9 DOGS

| Side of Graft Implantation | Follow-Up Days | Patency |
| --- | --- | --- |
| RFA | 3 | Patent |
| LCCA | 19 | Patent |
| RFA | 19 | Patent |
| RFA | 72 | Patent |
| RFA | 104 | Patent |
| LFA | 104 | Patent |
| RCCA | 121 | Patent |
| RFA | 186 | Occluded* |
| LFA | 186 | Patent |
| LFA | 196 | Patent |

TABLE 2-continued

SUMMARY OF 16 HSC-PBVG IMPLANTED IN 9 DOGS

| Side of Graft Implantation | Follow-Up Days | Patency |
|---|---|---|
| RFA | 196 | Patent |
| LCCA | 301 | Patent |
| LFA | 434 | Patent |
| LFA | 856+ | +Patent |
| RFA | 856+ | +Patent |
| Aorta | 1361+ | +Patent |

RFA — right femoral artery
LFA — left femoral artery
RCCA — right common carotid artery
LCCA — left common carotid artery
*Occlusion during the first week post implantation
+ animal is alive - long term follow-up According to this invention, a procedure is provided for the manufacture of processed biological vascular and other biological material grafts in which a segment of artery or the like is rendered free of soluble macromolecular components which would be expected to induce an immune reaction in the new host yet the normal mechanical properties of the tissue segment are retained through preservation of the elastin and collagen framework.

Accordingly, the invention provides, vascular grafts of acceptable characteristics as determined by morphological, biochemical and mechanical testing techniques and preliminary in vivo testing performed through the implantation of 16 vascular biografts in 9 dogs, 15 of which have been 5 to 6 mm in diameter implanted in the carotid or femoral locations. The results are conclusive regarding the invention's utility with only one early thrombotic occlusion, no aneurysm formation with follow-up of up to three years and no graft calcification or inflammation detected on histological examination at follow-up to 434 days.

Although preferred embodiments of the invention have been described herein in detail, it will be understood by those skilled in the art that variations may be made thereto without departing from the spirit of the invention or the scope of the appended claims.

The embodiments of the invention in which an exclusive property of privilege is claimed are defined as follows:

1. A process for preparing biological material for implant in mammal's cardiovascular system, respiratory system or soft tissue by removing cellular membranes, nucleic acids, lipids and cytoplasmic components and forming an extracellular matrix having as major components collagens and elastins, said process comprising the following sequence of steps:
   (1) isolating from a suitable donor a desired tissue sample of said biological material;
   (2) extracting said tissue sample with a hypotonic buffer solution at a mild alkaline pH for rupturing cells of said tissue sample, said hypotonic buffer solution including active amounts of proteolytic inhibitors and active amounts of antibiotic;
   (3) extracting said tissue sample with a buffered solution having a high concentration of salt, said solution being at a mild alkaline pH and including a non-ionic detergent and the proteolytic inhibitors and active amounts of antibiotic;
   (4) subjecting said tissue sample to enzymatic digestion in a buffered saline solution, said enzymes consisting of purified protease-free deoxyribonuclease and ribonuclease;
   (5) extracting said tissue sample with an anionic detergent at a mild alkaline pH, and
   (6) storing said tissue sample in physiologic buffered solutions.

2. The process of claim 1, wherein said extraction solution of steps (2) and (3) include the antibiotics penicillin and streptomycin.

3. A process of claim 1, wherein said extraction solution is steps (2), (3) and (5) are each at a mild alkaline pH in the range of 7.5 to 9.5.

4. A process of claim 1, wherein said suitable donor is human, bovine, ovine, porcine or caprine.

5. A process of claim 4, wherein said tissue sample is selected from the group consisting of veins, arteries, pericardium, dura mater, ligaments, tendons, trachea and skin.

6. A process of claim 5, wherein said biological material for implant is used for prostheses in vascular grafts, heart valves, replacement ligaments and tendons, trachea and skin.

7. A process of claim 1, wherein said non-ionic detergent of step (3) is selected from the group consisting of octylphenoxy polyethoxyethanol, polyethoxyethanol lauryl ether, polyethoxyethanol sorbitan monolaureate and polyoxyethylene lauryl ether.

8. A process of claim 7, wherein said selected non-ionic detergent is octylphenoxy polyethoxyethanol.

9. A process of claim 1, wherein said anionic detergent is selected from the group consisting of a salt of a sulfated higher aliphatic alcohol, sulfonated alkane and sulfonated alkylarene containing from 7 to 22 carbon atoms in a branched or unbranched chain.

10. A process of claim 9, wherein said anionic detergent is sodium dodecyl sulfate.

11. A process of claim 1, wherein said high salt concentration in said solution of step (3) is in the range of 1 to 2M of a desired physiological acceptable salt.

12. A process of claim 11, wherein said desired salt is KCl.

13. A process of claim 1, wherein said extraction solution of steps (2) and (3) include the protease inhibitors ethylenediaminetetraacetic acid and phenylmethylsulfonylfluoride.

14. A process of claim 1, wherein said extraction solution of steps (2) and (3) include the protease inhibitors ethylenediaminetetraacetic acid and phenylmethylsulfonylfluoride.

15. A process of claim 1, wherein steps (2) and (3) are carried out at a temperature in the range of 2° to 10° C.

* * * * *